United States Patent
Iori et al.

(10) Patent No.: US 6,893,126 B2
(45) Date of Patent: May 17, 2005

(54) OPTICAL SHEET FOR USE IN MANUFACTURING A CYLINDRICALLY SHAPED OPTICALLY CORRECT VISOR AND METHOD OF MANUFACTURING SAID VISOR

(75) Inventors: Giuseppe Iori, Reggio Emilia (IT); Federico Menta, Parma (IT); Matteo Lagasi, Bangkok (TH); Gian Giuseppe Giani, Parma (IT)

(73) Assignee: Intercast USA, Inc., Plymouth, MA (US)

( * ) Notice: Subject to any disclaimer, the term of this patent is extended or adjusted under 35 U.S.C. 154(b) by 0 days.

(21) Appl. No.: 10/717,150

(22) Filed: Nov. 18, 2003

(65) Prior Publication Data

US 2004/0156115 A1   Aug. 12, 2004

Related U.S. Application Data

(60) Provisional application No. 60/427,257, filed on Nov. 18, 2002.

(51) Int. Cl.$^7$ .............................................. G02C 7/02
(52) U.S. Cl. ...................... 351/159; 351/41; 351/177
(58) Field of Search ........................... 351/159, 41, 177

(56) References Cited

U.S. PATENT DOCUMENTS 4,547,049 A * 10/1985 Cotie ......................... 351/159
6,010,217 A *  1/2000 Houston et al. ............ 351/159

FOREIGN PATENT DOCUMENTS

WO        WO 97/03579           2/1997

* cited by examiner

*Primary Examiner*—Scott J. Sugarman
(74) *Attorney, Agent, or Firm*—Stroock & Stroock & Lavan LLP

(57) ABSTRACT

A plano-convex optical sheet having a positive power including:
  a substantially planar inner surface;
  opposed lateral edges, and
  a thickness s that is decreasing proceeding from a transversal central line passing through the geometric center of the optical sheet towards said opposed lateral edges along a portion of predetermined width w of the optical sheet, so as to define a convex outer surface having a curvature such that the optical sheet is capable of providing once bent a cylindrically shaped optically correct visor.

10 Claims, 5 Drawing Sheets

OPTICAL SHEET FOR USE IN MANUFACTURING A CYLINDRICALLY SHAPED OPTICALLY CORRECT VISOR AND METHOD OF MANUFACTURING SAID VISOR

CROSS-REFERENCE TO RELATED APPLICATIONS

This application claims the benefit of U.S. Provisional Application Ser. No. 60/427,257, filed on Nov. 18, 2002, entitled Cylindrically Shaped Optically Correct Visor, hereby incorporated by reference.

FIELD OF THE INVENTION

In a general aspect, the present invention relates to an optical sheet for use in manufacturing a cylindrically shaped optically correct visor.

More particularly, the invention relates to a transparent optical sheet for optical applications, preferably but not exclusively made of plastics, comprising a substantially planar inner surface and opposed lateral edges.

The cylindrically shaped optically correct visor obtainable from such an optical sheet may in turn be used to manufacture eyewear devices such as helmet shields, sunglasses, goggles and the like.

BACKGROUND OF THE INVENTION

It is well known that in some eyewear devices the visor included therein generally has a cylindrical shape.

One way to obtain such a shape, especially used in case of the most common thermoplastic optical materials such as polycarbonate, polymethylmethacrylate or polyamides, is to manufacture the visor by injection molding in an optically compensated mold.

A visor obtained in this way is described for example in International patent application WO 97/03579.

Although this technique may allow to manufacture a cylindrically shaped visor having the required optical characteristics, the investment costs to set up the necessary injection molding equipment are so high that they are generally justified only in case of mass-production of a large number of pieces, i.e. can be afforded only by large enterprises.

In case of smaller productions or whenever it is not economically affordable the use of such an expensive technique, sheet thermoforming still remains the only feasible method of manufacturing visors.

Nowadays, this technique is commonly carried out by thermoforming an optical sheet made of plastics material having two parallel surfaces, i.e. by thermoforming a plano-parallel optical sheet. The visors thus obtained are used for example in sport goggles, helmets and in certain models of fashion sunglasses.

More precisely and as best shown in FIGS. 1 and 2, a cylindrically shaped visor 4 is obtained from an optical sheet 1 having two parallel inner and outer surfaces 2, 3 by cutting the optical sheet 1 in shape, heating it at the softening temperature, bending it with the right curvature, cooling it down to a room temperature so as to obtain a visor 4 which is then mounted or fastened, for example, on the frame on the helmet temples.

However, the cylindrically shaped visor obtained in this way is not optically correct since the bending operation of the optical sheet 1 induces a negative optical power that can be easily measured with a telescope commonly present in any optical lab.

The reason for the negative optical power is that the light rays (shown by the arrows in FIG. 2) diverge when they pass through the two cylindrical concentric surfaces 2, 3. This negative power increases as the thickness of the optical sheet 1 increases and/or when the refractive index of the material constituting the same is increased and/or when the curvature of the final visor to be obtained is increased.

For example, if a 1.3 mm thick plano-parallel optical sheet 1 made of diethylenglycol-bis-allyl-carbonate (better known under the trade name of CR39®) with a refractive index of 1.523 is bent with a curvature radius of 87 mm (base 6), a negative spherical aberration of about −0.08 diopter (D) results.

If the thickness is increased to about 2 mm and/or the refractive index is higher than 1.523, the negative power becomes higher and the visor obtained will easily exceed the maximum value allowed by the international standards for sunglass lenses (for example −0.09D for Optical Class 1 defined by the European Standard EN 1836).

Accordingly, the cheaper thermoforming technique has been used—to date—only to manufacture cylindrically shaped non optically correct visors having a maximum thickness of about 2 mm.

SUMMARY OF THE INVENTION

According to the present invention, it has now been found that it is possible to overcome the limitations inherent to the economically desirable thermoforming technique and to provide a cylindrically shaped optically correct visor for use in eyewear having the same optical characteristics of a visor obtained by the more expensive technique of injection molding, by applying this bending technique to an optical sheet having a predetermined varying thickness along its width.

According to a first aspect, the present invention provides a plano-convex optical sheet having a variable thickness or non-parallel surfaces.

According to the invention, it has been found that the plano-convex optical sheet having the defined predetermined variable thickness characteristics is capable—once bent—to provide the right compensation at any desired point of any horizontal line parallel to the median line of the visor, i.e. of any horizontal line parallel to the upper and lower edges of the visor itself.

In the following description and in the appended claims, the term: median line of the optical sheet or of the visor, is intended to indicate a horizontal line passing through the geometric center of the sheet or of the visor itself in its use conditions.

According to the invention, the thickness of the optical sheet decreases proceeding from a transversal central line passing through the geometric center of the optical sheet towards the opposed lateral edges thereof along a portion of predetermined width.

According to a first preferred embodiment of the invention, the thickness of the optical sheet decreases from the aforementioned transversal central line towards said opposed lateral edges along substantially the total width of the optical sheet.

According to an alternative preferred embodiment of the invention, the thickness of the optical sheet decreases from said transversal central line towards said opposed lateral edges along a portion of the optical sheet having a predetermined width lower than the total width of the optical sheet.

Within the framework of this embodiment, therefore, the optical sheet will include two substantially plano-parallel lateral portions near the opposed lateral edges thereof.

In a first variant of this alternative preferred embodiment of the invention, the thickness of the optical sheet decreases from said transversal central line towards said opposed lateral edges along a portion of the optical sheet having a width adapted to include, once bent, substantially the entire field of lateral vision allowed by the visor to be obtained.

In this way, it is advantageously possible to obtain a cylindrically shaped visor which is optically correct along the portion thereof which is actually exploited by the wearer during the normal use conditions of the visor, i.e. it is not unnecessary wide.

In a second variant of this alternative preferred embodiment of the invention, the thickness of the optical sheet decreases from the transversal central line towards said opposed lateral edges along a portion of the optical sheet having a width comprised between about 84 and about 500 mm, more preferably comprised between about 100 and about 340 mm.

According to a second aspect, the present invention provides a method of manufacturing a cylindrically shaped optically correct visor as is defined in attached claim 8.

Most advantageously, the method of manufacture of the invention allows to obtain with a very cheap technique and at low investment costs a cylindrically shaped optically correct visor having substantially any desired thickness from a plano-convex optical sheet having a variable thickness or non-parallel surfaces.

Most advantageously, the cylindrically shaped optically correct visor thus obtained is capable to provide—regardless of its maximum thickness—the right compensation at any desired point of any horizontal line parallel to the median line thereof, i.e. of any horizontal line parallel to the upper and lower edges of the visor itself.

Other objects and features of the present invention will become apparent from the following detailed description, considered in conjunction with the accompanying drawing figures. It is to be understood, however, that the drawings are designed solely for the purpose of illustration and not as a definition of the limits of the invention, for which reference should be made to the appended claims.

BRIEF DESCRIPTION OF THE DRAWINGS

In the drawing figures, which are not to scale, and which are merely illustrative.

DETAILED DESCRIPTION OF THE PREFERRED EMBODIMENTS

Figure 1:
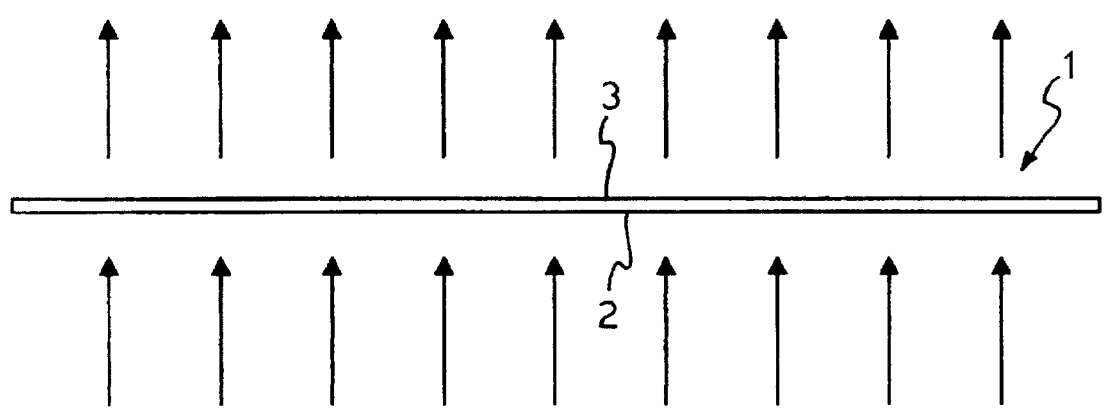
FIG. 1 is a cross sectional view of a sheet of optical material constructed in accordance with the prior art.
Figure 2:
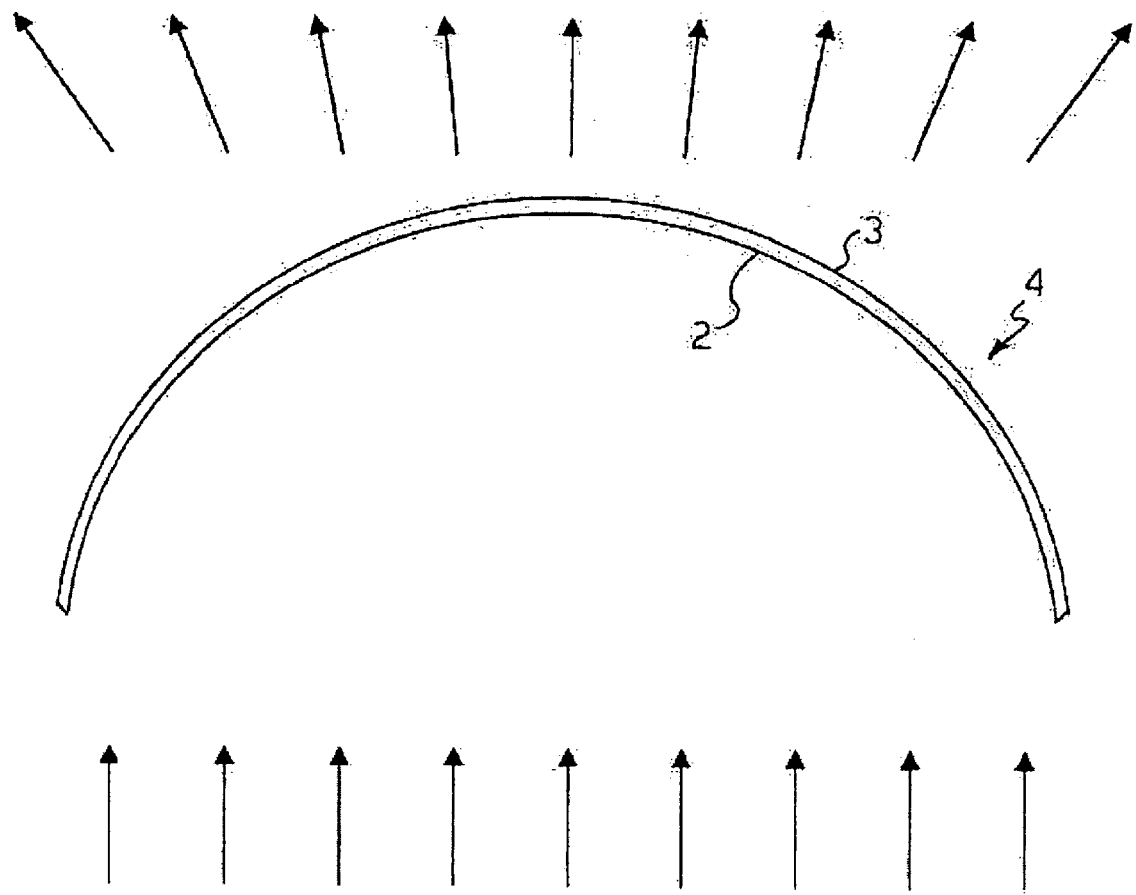
FIG. 2 is a cross sectional view of the optical sheet depicted in FIG. 1 bent in a cylindrical shape.
Figure 3:
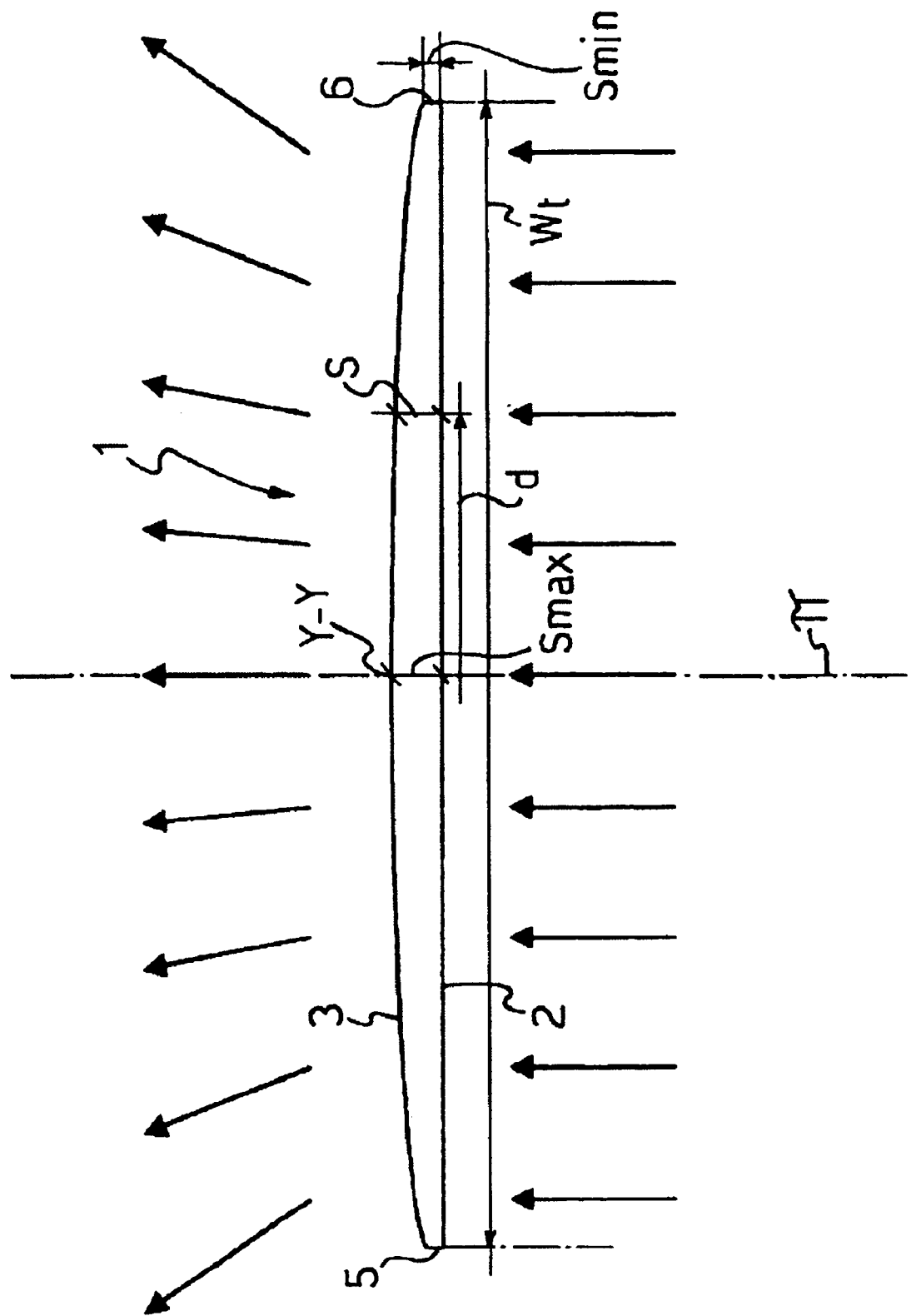
FIG. 3 is a cross sectional view of a sheet of optical material constructed in accordance with the present invention.
Figure 4:
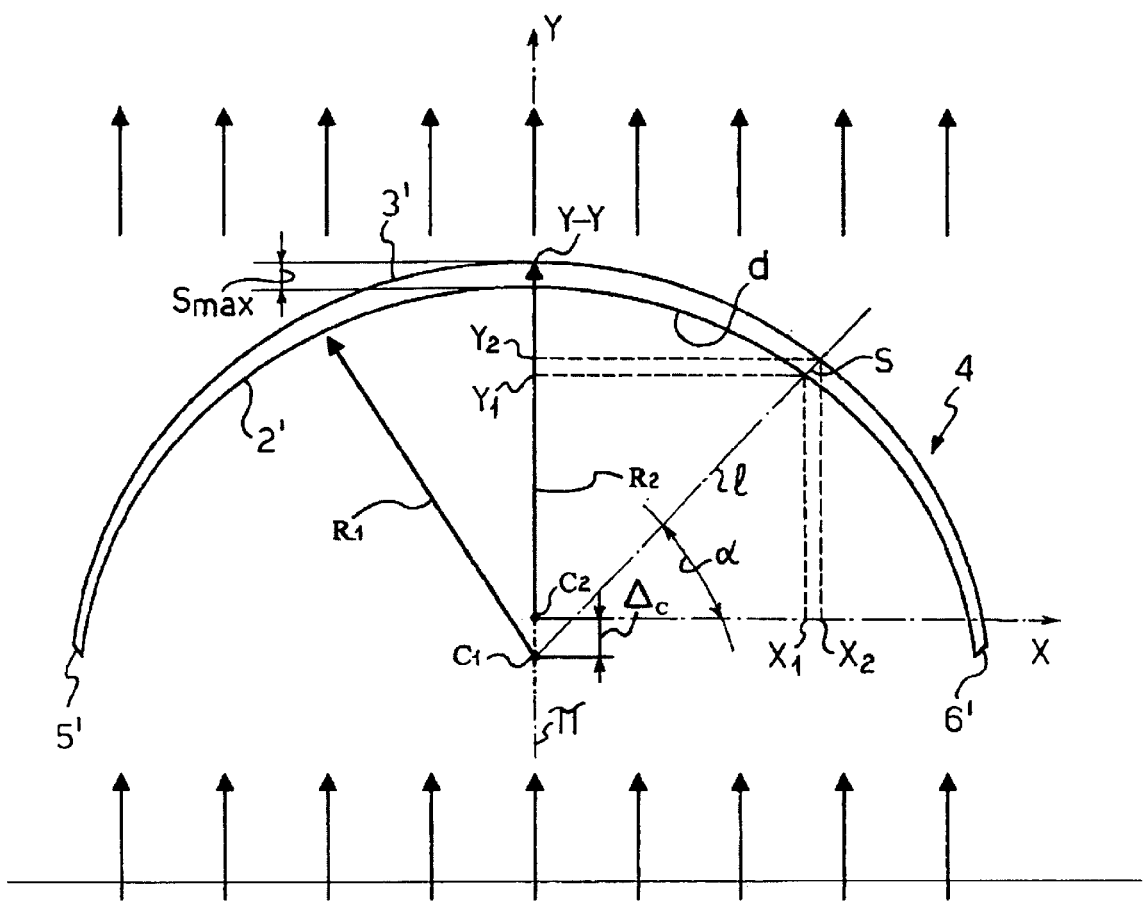
FIG. 4 is a cross sectional view of a cylindrically shaped optically correct visor obtained by bending in a cylindrical shape the optical sheet depicted in FIG. 3.

With reference to FIGS. 3 and 4, an optical sheet according to a preferred embodiment of the invention, which in the specific example is made of transparent plastics material, is generally indicated at 1.

The optical sheet 1 is substantially parallelepipedic and includes a substantially planar inner surface 2, opposed lateral edges 5, 6 and opposed upper and lower edges not visible in the figures.

The plastics materials of most preferred and advantageous use are those selected from the group comprising: polymethyl methacrylate, polyol-allyl-carbonates, aromatic polycarbonates, polystyrene, cellulose esters, polyacrylates, polyalkylacrylates, polyurethanes, saturated and unsaturated polyesters, transparent polyamides, and mixtures thereof.

Among them, polyurethane castable elastomers, sold under the trade names of NXT® or TRIVEX®, and diethylenglycol-bis-allyl-carbonate sold under the trade name of CR39®, commonly used for the manufacture of visors and oculars, such as for instance visors for helmets and lenses (either ophthalmic or not) for eyeglasses, are preferred.

In the alternative, the optical element may be also made of copolymers of the above polymers with other monomers suitable for the purpose, such as for instance, methyl-methacrylate, maleic anhydride, triallyl-cyanide and vinyl acetate.

According to the invention, the thickness of the optical sheet 1 decreases proceeding from a transversal central line Y—Y passing through the geometric center of the optical sheet 1, at which the optical sheet 1 has a maximum thickness $s_{max}$, towards the opposed lateral edges 5, 6, at which the optical sheet 1 has a minimum thickness $s_{min}$, along a portion of predetermined width w of the optical sheet 1 (FIG. 3).

Figure 5:
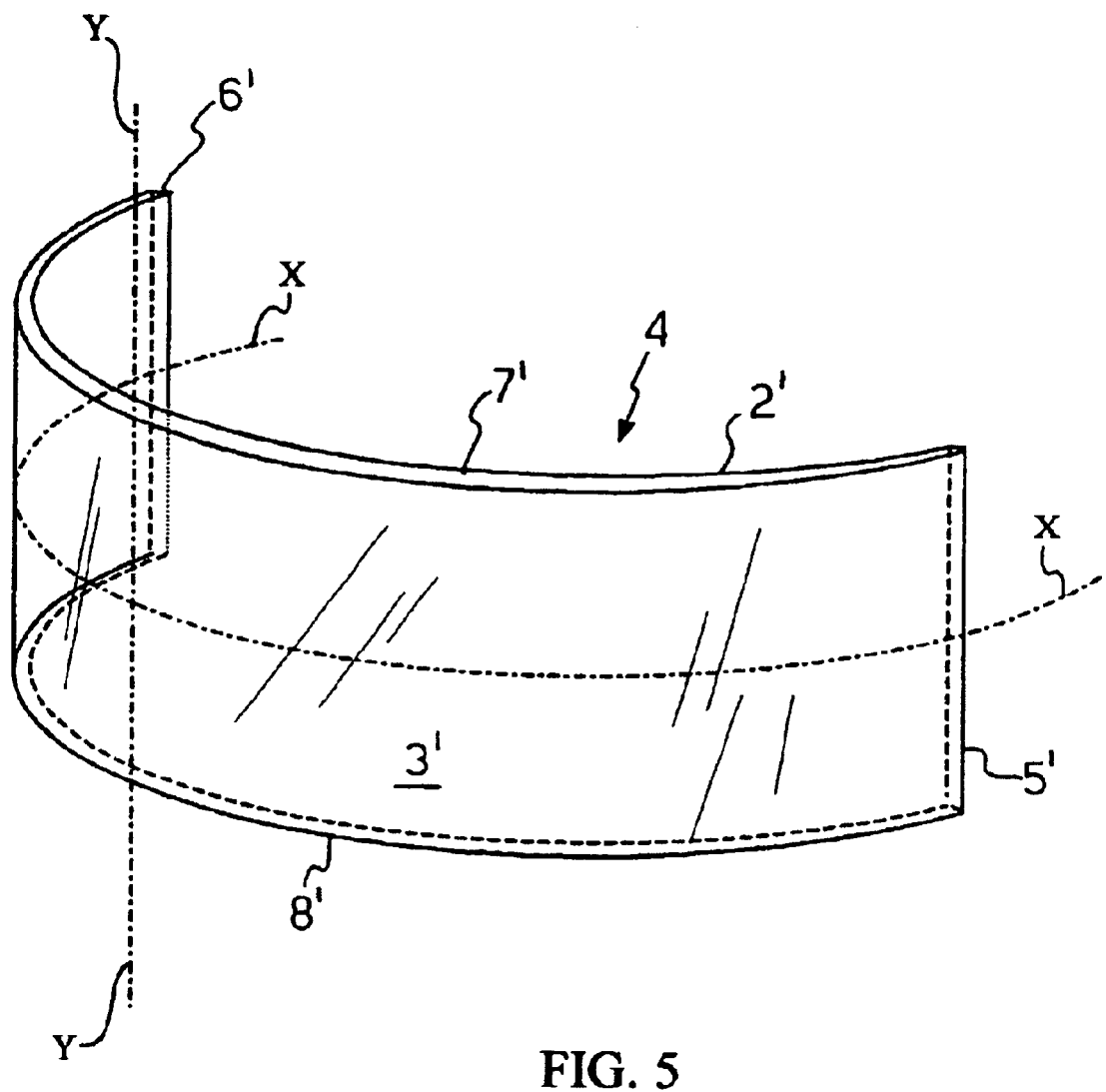
FIG. 5 is a perspective view of the cylindrically shaped optically correct visor depicted in FIG. 3.

Thanks to this feature, a convex outer surface 3 is defined having a curvature such that the optical sheet 1 is capable of providing, once bent, a cylindrically shaped optically correct visor 4 shown in FIGS. 4 and 5.

In the preferred embodiment shown in FIG. 3, the thickness s of the optical sheet 1 decreases the transversal central line Y—Y towards the opposed lateral edges 5, 6 along substantially the total width wt of the optical sheet 1.

In the following description and in the appended claims, the term: transversal central line of the optical sheet 1 or of the visor 4 obtained therefrom, is intended to indicate a line Y—Y passing through the geometric center of the optical sheet 1 or of the visor 4 in its use conditions and substantially perpendicular to the upper and lower edges of the optical sheet or of the visor as best shown in FIGS. 3–5.

More specifically, the transversal central line Y—Y of the optical sheet 1 is defined on the outer surface 3 of the sheet 1 by a vertical plane p passing through the geometric center of the optical sheet 1, while the transversal central line Y—Y of the visor 4 is defined on the outer surface 3' of the visor 4 by a vertical plane p substantially parallel to the opposed lateral edges 5', 6' of the visor and passing through the centers of curvature C1, C2 of both the inner and outer surfaces 2', 3' of the visor 4.

In the following description and in the appended claims, the term: geometric center of the optical sheet 1 or of the visor 4 obtained therefrom, is intended to indicate the intersection of the diagonals of the smallest rectangle having at least one horizontal side and circumscribed to the optical sheet 1 or to the visor 4.

Within the framework of the present description, furthermore, width and height of the optical sheet 1 and of the visor 4 are intended to be measured along lines parallel to the horizontal median line X—X and, respectively, to the vertical transversal central line Y—Y thereof, as best shown in FIG. 5 which shows a visor 4 in its use conditions.

Preferably, the opposed lateral edges 5, 6 of the optical sheet 1 are substantially parallel to such a transversal central line Y—Y to give a truly cylindrical visor 4 after bending (see FIG. 5).

In a preferred embodiment, the maximum thickness $s_{max}$ of the optical sheet 1 at the transversal central line Y—Y is comprised between about 1 and about 5 mm, more preferably between about 1.8 and about 4 mm, while the minimum thickness $s_{min}$ at the opposed lateral edges 5, 6 of the sheet 1 is comprised between about 1 and about 3 mm, more preferably between about 1.5 and about 2.5 mm as a function of the desired degree of breaking, tensile or impact strength.

In a preferred embodiment, the width of the optical sheet 1 as measured along the median line X—X thereof is comprised between about 100 and about 550 mm, more preferably between about 150 and about 400 mm, as a function of the specific application requirement of the visor 4 to be obtained.

In a preferred embodiment, the height of the optical sheet 1 as measured along the transversal central line Y—Y thereof is comprised between about 45 and about 300 mm, more preferably between about 60 and about 250 mm, as a function of the specific application requirement of the visor 4 to be obtained.

Such an optical sheet 1 may be obtained with known techniques depending on the nature of the plastic materials.

Preferably, in the case of castable materials such as CR39® or cast polyurethanes, variable thickness sheets can be obtained by pouring the material into a mold formed by two glass sheets spaced by two lateral gaskets having the same cross-sectional shape, i.e. the same variable thickness, as that of the optical sheet to be obtained, or having a suitable cross-sectional shape, i.e. a variable thickness, designed so as to take account of the known shrinkage characteristics of the material used.

Preferably, in the case of thermoplastic materials like polycarbonate or polymethyl methacrylate (PMMA), polyamides and cellulosic polymers, the used techniques may be direct injection molding or extrusion in such a way to obtain an optical sheet 1, such as that shown in FIG. 3, having a thickness decreasing proceeding from the transversal central line Y—Y towards the opposed lateral edges 5, 6 along a portion of predetermined width w of the optical sheet 1.

Said in another way, the optical sheet 1 has a thickness that increases proceeding from one lateral edge 5 to the transversal central line Y—Y and than decreases again to the other lateral edge 6 and this along a portion of predetermined width w of the optical sheet 1.

Accordingly, the optical sheet 1 includes a substantially plano-convex portion which has—as such—a positive power that is annulled when the optical sheet is bent to an appropriate curvature.

As used herein, the term: positive power, means that the optical sheet 1 or any substantially plano-convex portion thereof acts as a positive lens that converges the rays toward a focus.

The positive power of the variable thickness of optical sheet 1 or of any substantially plano-convex portion thereof is substantially annulled by cylindrical bending of the sheet itself as will be explained hereinafter.

In the preferred embodiment shown in FIG. 3, the convex outer surface 3 of the whole optical sheet 1 has a curvature such that the optical sheet 1 is capable of providing, once bent, a cylindrically shaped optically correct visor 4 which will be described in more detail hereinbelow.

Most advantageously, the visor 4 is capable to provide the right compensation at any desired point of any horizontal line parallel to its median line X—X, i.e. of any horizontal line parallel to the upper and lower edges 7', 8' of the visor itself.

More specifically, as shown in FIG. 4, which is a cross sectional view of the visor 4 of FIG. 5 taken along the median line X—X thereof, the visor 4 has a thickness "s" along its entire arc length, which is defined between an outer (convex) surface 3' having a radius R2 and an inner (concave) surface 2' having a radius R1.

The radius R1 is less than the radius R2 and eccentric relative thereto.

Specifically, the surfaces 2' and 3' have different radii of curvatures R1, R2 about centers C1, C2 that are shifted relative to each other.

This eccentricity shifts one surface with respect to the other, to create a cylindrical visor 4 which has a thickness "s" that decreases proceeding from a transversal central line Y—Y at which the optical visor 4 has a maximum thickness $s_{max}$ equal to the maximum thickness of the optical sheet 1, towards the opposed lateral edges 5', 6' at which the visor 4 has a minimum thickness $s_{min}$, just in the same way as for the optical sheet 1 described hereinabove.

As illustrated, the distance ΔC between the center of curvature C1 for radius R1 and the center of curvature C2 for radius R2 is lower than the difference ΔR=R2−R1 between the radii of curvature.

The distance ΔC may be determined by those of ordinary skill in the art on the basis of the following relation:

$$\Delta C = s_{max} - \Delta R$$

This distance can thus vary depending upon the desired thickness $s_{max}$ of the visor 4 at the transversal central line Y—Y or upon the desired thickness $s_{min}$ of the visor 4 at the opposed lateral edges 5', 6'.

As said above, the thickness of the optical sheet 1 decreases from the transversal central line Y—Y at which the optical sheet 1 has a maximum thickness $s_{max}$, towards the opposed lateral edges 5, 6 at which the optical sheet 1 has a minimum thickness $s_{min}$.

In a preferred embodiment, such a cylindrically shaped optically correct visor 4 may be obtained by bending an optical sheet 1 having a thickness "s" which varies starting from the transversal central line Y—Y towards the opposed lateral edges 5, 6 in accordance with the following equations:

$$s^2 = (x_2 - x_1)^2 + (y_2 - y_1)^2 \qquad (I)$$

$$d = (\pi - \alpha) \cdot R1 \qquad (II)$$

wherein:

s is the thickness of the optical sheet 1 at a point having a distance d from the transversal central line Y—Y as measured along the inner surface 2 of the optical sheet 1;

d is accordingly the distance from the transversal central line Y—Y as measured along the inner surface 2 of the optical sheet 1 of a point for which the thickness s is to be determined; in FIG. 4, the distance d corresponds to the length of the arc of a circle spanning from the transversal central line Y—Y to a given point of coordinates $x_1, y_1$ lying on the inner surface 2' of the visor 4;

$x_1$, $y_1$, are the Cartesian coordinates, in a Cartesian plane having its origin at the center of curvature C2 of the outer surface 3' of the visor 4 to be obtained, of a point having a distance d as measured along the inner surface 2' of the final visor 4 to be obtained from the transversal central line Y—Y (i.e. as measured along an arc of a circle of radius R1);

$x_2$, $y_2$ are the Cartesian coordinates, in the aforementioned Cartesian plane having its origin at the center of curvature C2 of the outer surface 3' of the visor 4 to be obtained, of a point lying on the outer surface 3' of the final visor 4 to be obtained and on the same straight line 1 passing through the center of curvature C1 and point of coordinates $x_1$, $y_1$.

The values of the Cartesian coordinates x1, y1 are determined by the following equations:

$$x_1 = R1 \cdot \cos \alpha \quad \text{(III)}$$

$$y_1 = R1 \cdot \sin \alpha - \Delta C \quad \text{(IV)}$$

wherein:

R1 is the radius of curvature of the inner surface 2' of the visor 4 to be obtained;

ΔC is the distance between the two centers of curvature C1 and C2 of the inner and outer surfaces 2', 3' of the visor 4 as measured along the y-axis of the Cartesian coordinates x, y defined above;

α is the angle defined by the straight line 1 passing through the center of curvature C1 and points of coordinates $x_1$, $y_1$, and $x_2$, $y_2$ in the aforementioned Cartesian plane.

The values of the Cartesian coordinates $x_2$, $y_2$ are in turn determined by solving the following system of equations:

$$x_2^2 + y_2^2 = R_2^2 \quad \text{(V)}$$

$$y_2 = \tan \alpha \cdot x_2 + \Delta C \quad \text{(VI)}$$

wherein:

R2 is the radius of curvature of the outer surface 3' of the visor 4 to be obtained, while α and ΔC are as defined above.

By solving this system, it follows that $$x_2 = \frac{-\Delta C \cdot \tan g\alpha \pm R2 \cdot (\tan g^2\alpha - \Delta C^2 / R_2^2 + 1)^{1/2}}{\tan g^2 \alpha + 1}$$

$$y_2 = \frac{\Delta C \cdot \tan g^2 \alpha \pm R2 \cdot \tan g\alpha \cdot (\tan g^2\alpha - \Delta C^2 / R_2^2 + 1)^{1/2}}{\tan g^2 \alpha + 1} + \Delta C$$

wherein: R2, α and ΔC are as defined above.

In view of the fact that for a given cylindrically shaped optically correct visor 4 to be produced the maximum thickness $s_{max}$ at the transversal central line Y—Y, the radius of curvature R2 of the outer surface 3' (or base) and the refractive index n of the material used are known design parameters, it follows that the radius of curvature R1 of the inner surface 2' may be calculated as follows:

$$1/R1 = \frac{1/R2}{1 - [s_{max} \cdot 1/R2 \cdot (n-1)/n]}$$

while ΔC may be calculated—as said above—by subtracting ΔR from the maximum thickness $s_{max}$ at the transversal central line Y—Y.

In this regard, it is finally to be noted that the radius of curvature R2 of the outer surface 3' of the visor 4 may be calculated as a function of the selected base from the following relation:

$$523/\text{base} = R2$$

wherein 523 is by convention the decimal part of the refraction index n of glass and "base" is the parameter which determines the curvature of the outer surface 3' of the visor 4.

The cylindrically shaped optically correct visor 4 obtainable from the optical sheet 1 of the present invention may advantageously be an Optical Class 1 visor according to European Standard EN 1836 for use in eyewear.

In particular, the cylindrically shaped optically correct visor 4 may be used to advantage in helmet shields, sunglasses, goggles and the like.

In accordance with the invention, the aforementioned cylindrically shaped optically correct visor 4 may be manufactured by a method comprising the step of:

a) providing a plano-convex optical sheet 1 having a positive power as described above;

b) bending the optical sheet 1 to an appropriate curvature so as to annul its positive power.

Preferably, step b) is carried out by first heating the optical sheet 1 at a temperature above the softening temperature thereof and then by bending the heated sheet using known apparatuses, such as a molding apparatus having a predetermined curvature.

Still more preferably, step b) is carried out by heating the optical sheet 1 at a temperature comprised between 100° and 170° C. using known apparatuses, such as an air oven.

Preferably, step b) is carried out so that said predetermined curvature is such that the curvature radius R2 of the outer surface 3' of the visor 4 is comprised between base 2 and base 12.

According to a preferred alternative embodiment, the method of the invention may further comprise, if desired, the step of cutting the bent optical sheet 1 obtained from step b) along two cutting lines substantially parallel to the transversal central line Y—Y and positioned at different distances therefrom.

In this way, it may advantageously be obtained a visor 4 having a different thickness s at the opposed lateral edges 5', 6' thereof in order to fulfill specific application requirements.

In an example of the method of the invention, a cylindrical visor 4 with 0 power, i.e. an optically neutral visor belonging to Optical Class 1, may be manufactured from a substantially parallelepipedic optical sheet 1 made of plastic transparent material (like NXT® or CR39®) having the following dimensions: 400 mm wide and 150 mm high, with a thickness $s_{min}$ of about 1.1 mm at the two opposed lateral edges 5, 6.

Such an exemplary optical sheet 1 may have a maximum thickness $s_{max}$ at the transversal central line Y—Y of about 3.0 mm which then decreases in accordance with the preferred law of variation defined above down to the aforementioned value of about 1.1 mm at the opposite lateral edges 5, 6.

This sheet 1 shows per se a positive optical power as may be determined by examining the same by means of a telescope, because of its variable thickness along its width.

This positive optical power lowers up to becoming zero at a certain degree of curvature as shown by FIGS. 3 and 4. The curvature for the visor 4 obtained in this case will be around base 4 (523/4=R2=130.75 mm). If a stronger curvature (base 6, 7, 8, 9 etc.) is needed, the thickness $s_{max}$ at the transversal central line Y—Y of the sheet 1 has to increase accordingly.

This rule is valid for any optical material and depends only on the refractive index n and on the cylindrical curvature or base which is desired.

Thus, while there have been shown and described and pointed out novel features of the present invention as applied to preferred embodiments thereof, it will be understood that various omissions and substitutions and changes in the form and details of the disclosed invention may be made by those skilled in the art without departing from the spirit of the invention. It is the intention, therefore, to be limited only as indicated by the scope of the claims appended hereto.

It is also to be understood that the following claims are intended to cover all of the generic and specific features of the invention herein described and all statements of the scope of the invention which, as a matter of language, might be said to fall there between. In particular, this invention should not be construed as being limited to the dimensions, proportions or arrangements disclosed herein.

We claim:

1. A plano-convex optical sheet having a positive power including:
   a substantially planar inner surface;
   opposed lateral edges, and
   a thickness s that is decreasing proceeding from a transversal central line passing through the geometric center of the optical sheet towards said opposed lateral edges along a portion of predetermined width w of the optical sheet, so as to define a convex outer surface having a curvature such that the optical sheet is capable of providing once bent a cylindrically shaped optically correct visor;
   wherein the thickness s of the sheet decreases from said transversal central line towards said opposed lateral edges in accordance with the following equation:

$$s^2 = (x_2-x_1)^2 + (y_2-y_1)^2$$
$$d = (\pi-\alpha)R1$$

wherein:
   s is the thickness of the optical sheet at a point having a distance d from the transversal central line as measured along the inner surface of the optical sheet;
   d is the distance from the transversal central line as measured along the inner surface of the optical sheet at a point of thickness s;
   $x_1$, $y_1$ are the Cartesian coordinates, in a Cartesian plane having its origin at the center of curvature C2 of an outer surface of the visor to be obtained, of a point having a distance d as measured alone the inner surface of the visor to be obtained from the transversal central line;
   $x_2$, $y_2$ are the Cartesian coordinates, in said Cartesian plane, of a point lying on the outer surface of the final visor to be obtained and on the same straight line 1 passing through the center of curvature C1 and a point of coordinates $x_1$, $y_1$;
   R1 is the radius of curvature of the inner surface of the visor as defined by the following equation:

$$1/R1 = \frac{1/R2}{1 - [s_{max} \cdot 1/R2 \cdot (n-1)/n]}$$

wherein
   R2 is the radius of curvature of the outer surface of the visor;
   $S_{max}$ is the maximum thickness of the optical sheet at the transversal central line;
   n is the refraction index of the optical sheet;
   $\alpha$ is the angle defined by the straight line 1 passing through the center of curvature C1 and points $x_1$, $y_1$ and $x_2$, $y_2$ in the said Cartesian plane of coordinates.

2. A plano-convex optical sheet according to claim 1, wherein the thickness s of the optical sheet decreases from said transversal central line towards said opposed lateral edges along substantially the total width wt of the optical sheet.

3. A plano-convex optical sheet according to claim 1, wherein the thickness s of the optical sheet decreases from said transversal central line towards said opposed lateral edges along a portion of the optical sheet having a width w adapted to include, once bent, substantially the entire field of lateral vision allowed by the visor.

4. A plano-convex optical sheet according to claim 1, wherein the thickness s of the optical sheet decreases from said transversal central line towards said opposed lateral edges along a portion of the optical sheet having a width w comprised between about 84 and about 500 mm.

5. A plano-convex optical sheet according to claim 1, having a maximum thickness $S_{max}$ along said transversal central line comprised between about 1 and about 5 mm.

6. A plano-convex optical sheet according to claim 1, having a minimum thickness $S_{min}$ at said opposed lateral edges comprised between about 1 and about 3 mm.

7. A method of manufacturing a cylindrically shaped optically correct visor comprising the steps of:
   a) providing a plano-convex optical sheet having a positive power;
   b) bending said sheet to an appropriate curvature so as to annul the positive power of said sheet;
   wherein the thickness s of the sheet decreases from said transversal central line towards said opposed lateral edges in accordance with the following equation:

$$s^2 = (x_2-x_1)^2 + (y_2-y_1)^2$$
$$d = (\pi-\alpha)R1$$

wherein:
   s is the thickness of the optical sheet at a point having a distance d from the transversal central line as measured along the inner surface of the optical sheet;
   d is the distance from the transversal central line as measured along the inner surface of the optical sheet at a point of thickness s;
   $x_1$, $y_1$ are the Cartesian coordinates, in a Cartesian plane having its origin at the center of curvature C2 of an outer surface of the visor to be obtained, of a point having a distance d as measured along the inner surface of the visor to be obtained from the transversal central line;
   $x_2$, $y_2$ are the Cartesian coordinates, in said Cartesian plane, of a point lying on the outer surface of the final visor to be obtained and on the same straight line 1 passing through the center of curvature C1 and a point of coordinates $x_1$, $y_1$;
   R1 is the radius of curvature of the inner surface of the visor as defined by the following equation:

$$1/R1 = \frac{1/R2}{1 - [s_{max} \cdot 1/R2 \cdot (n-1)/n]}$$

wherein
   R2 is the radius of curvature of the outer surface of the visor;
   $s_{max}$ is the maximum thickness of the optical sheet at the transversal central line;
   n is the refraction index of the optical sheet;
   $\alpha$ is the angle defined by the straight line 1 passing through the center of curvature C1 and points $x_1$, $y_1$ and $x_2$, $y_2$ in the said Cartesian plane of coordinates.

8. A method according to claim 7, wherein said step b) is carried out by heating said sheet at a temperature above the softening temperature thereof and by bending the heated sheet in a molding apparatus having a predetermined curvature.

9. A method according to claim 7, wherein said predetermined curvature is such that the curvature radius R2 of the outer surface of the visor is comprised between base 2 and base 12.

10. A method according to claim 7, further comprising the step of cutting the bent optical sheet obtained from step b) along two cutting lines substantially parallel to said transversal central line and positioned at different distances therefrom, so as to obtain a visor having a different thickness s at opposed lateral edges thereof.

* * * * *